Figure 1:
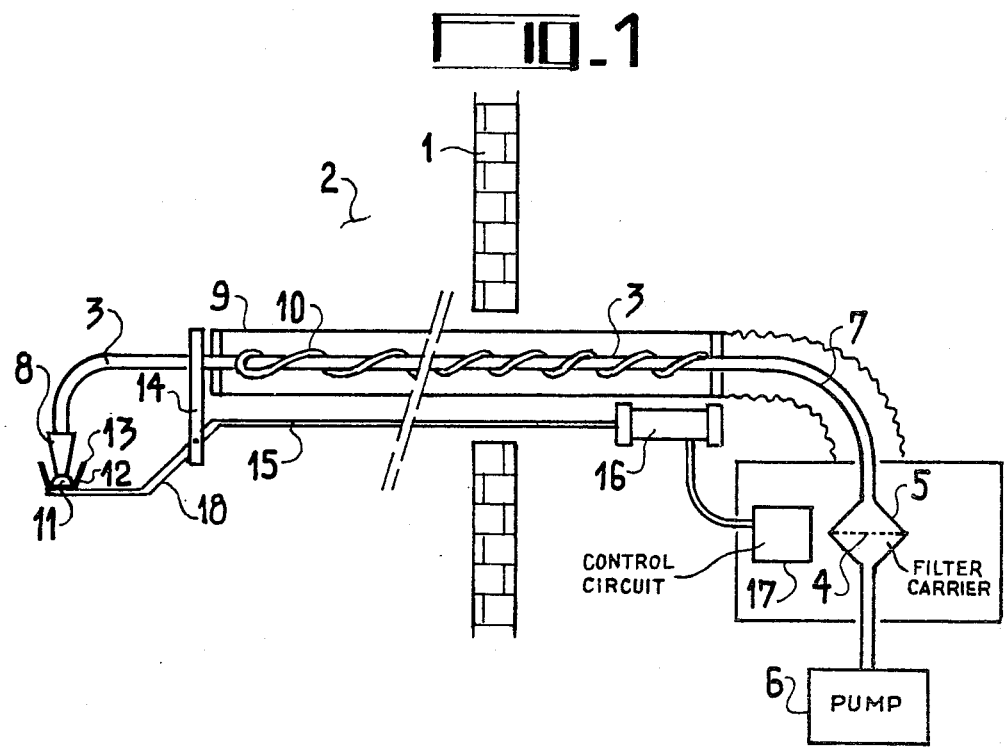

United States Patent [19]

d'Auzac et al.

[11] 4,140,006
[45] Feb. 20, 1979

[54] DEVICE FOR TAKING SAMPLES OF DUST IN A GAS FLOW

[75] Inventors: Gerard d'Auzac; Joseph Majerowicz, both of Massy, France

[73] Assignee: Saphymo-Stel, Massy, France

[21] Appl. No.: 884,749

[22] Filed: Mar. 9, 1978

Related U.S. Application Data

[63] Continuation of Ser. No. 748,782, Dec. 7, 1976, abandoned.

[30] Foreign Application Priority Data

Dec. 9, 1975 [FR] France ................... 75 37665

[51] Int. Cl.² .................. G01N 1/22; B01D 53/30
[52] U.S. Cl. .................... 73/28; 73/421.5 A
[58] Field of Search ............. 73/28, 421.5 A, 421.5 R; 55/270

[56] References Cited

U.S. PATENT DOCUMENTS

| | | | |
|---|---|---|---|
| 2,484,202 | 10/1949 | Wintermute | 73/28 |
| 3,229,526 | 1/1966 | Kennedy | 73/421.5 A |
| 3,794,909 | 2/1974 | Smith | 73/28 |
| 3,803,920 | 4/1974 | Homolya et al. | 73/421.5 R |
| 3,841,145 | 10/1974 | Boubel | 73/28 |

OTHER PUBLICATIONS

Simpson, "A Fast Gas Valve for Plasma Sampling," *Journal of Physics,* vol. 8, No. 9, pp. 739–741, Sep. 1975.

*Primary Examiner*—Stephen A. Kreitman
*Attorney, Agent, or Firm*—Edwin E. Greigg

[57] ABSTRACT

A device for taking samples of dust in a pipe or a chimney discharging gases, into the atmosphere.

The device permits completely emptying the sampling tube of the dusts to be measured by means for rapidly and briefly closing the orifice of the sampling tube, which produces, once or several times during each sampling period, a pneumatic shock in the sampling tube which is subjected to pumping.

Such a device permits effecting particularly precise measurements of the concentration of dust by weight. It also permits a continuous utilization of the device during very long periods of time without its clogging up.

5 Claims, 2 Drawing Figures

DEVICE FOR TAKING SAMPLES OF DUST IN A GAS FLOW

This is a continuation, of application Ser. No. 748,782 filed Dec. 7, 1976, now abandoned The present invention relates to an improved device for taking samples of dust or pulverous materials in enclosures or chambers, wherein it is desired to measure the density or content of these materials, these enclosures being, for example, chimneys which discharge dust into to the atmosphere or exhaust pipes for gases charged with dusts.

As dusts are acknowledged to be one of the most dangerous atmospheric pollutants, it is necessary to measure the dust content of gases emitted into the atmosphere with high precision, in particular of course at their sources, such as the outlets of chimneys or gas discharging pipes. This measuring of the concentrations by weight of dusts in gases discharged into the atmosphere is governed by severe regulations in most countries.

Moreover, this measuring of the concentrations of the discharged dusts may help to determine the efficiency of the filtering process of dust reduction and its eventual deterioration.

A conventional process employed for measuring concentration consists in taking a sample of gass in the pipe, collecting the dust contained therein on a filter, measuring the mass of this dust -by weighting or any other known process- while measuring the volume and the flow of the sampled gas. These two measurments of mass and volume require high precision.

In order to take the sample from inside the pipe and convey it to the filter, a tubular device termed a sampling tube or probe is employed, which may have a tength of as much as 3 meters or more. This sampling tube plays a determining part in the precision of the measurement.

The dust carried along by the gaseous flow in the sampling tube has a tendency to become deposited on the inner walls thereof by sedimentation or impaction.

Consequently, there is a loss of dust i.e. a portion thereof, which does not reach the filter, and a blackage of the sampling tube or a reduction of the diameter of its inlet nozzle may occur over a lapse of time, which will give rise to sampling errors, this diameter being of great importance in computing the dust content per unit volume.

The magnitude of the losses of masses of dust in the sampling tube depends on a very large number of factors such as: the state of the inner surface, temperature of the walls, rate of flow, nature of the dusts, particle size spectrum, etc.

Solutions have been proposed, such as the dilution of the sampled gases by the addition thereto of known additional flow of dust-free air. This device implies doubling the means for controlling and measuring the flow which is sampled in the chimney or exhaust pipe and poses serious problems of pressure drop. Its efficiency cannot be assured.

Another more elaborate solution consists in conveying the dust on a kind of air cushion. The suction pipe is then made from a porous material, for example a stainless steel of a given porosity. A supply of dust-free air is made to penetrate transpire through the pores of the wall and form inside the tube a layer of air in the shape of a sleeve which is such that the dusts are carried along the axis of the sampling pipe without contact with the wall. Such a device is costly and also requires the precise controlling of two flows.

The present invention concerns a device for taking samples of dusts in a pipe which, in addition to being particularly simple to construct and use, avoids the aforementioned drawbacks and in particular ensures that the sampled dust does not adhere to the inner walls of the sampling tube. The device according to the invention therefore avoids both inaccuracies in the measurement and danger of obstruction of the sampling tube.

According to the invention, there is provided a device for taking samples of dust from a pipe by means of a sampling tube which enters the pipe and through which the gases charged with dusts are drawn off, comprising : pumping means for drawing gas samples from the pipe, connected to the outlet end of the sampling tube; means for closing the inlet end of the sampling tube which is located inside the pipe, said closing means being actuated rapidly, one or more times during each sampling period, while the pumping means are operating, so as to produce within the sampling tube as may pneumatic shocks as there are closure, whereby preventing the deposition of dust on the inner sidewall of the sampling tube.

As any measurement effected by sampling a gas in a pipe comprises a pumping interval or sampling period proper, followed by an interval for extracting and changing the filter and measuring the dust which have been deposited thereon in the course of the pumping interval, the dust should not enter the tube outside the sampling periods.

According to another feature of the invention, the means for closing the inlet end will be controleed at the start and at the end of each sampling period so as to respectively open and close said mouth.

Figure 2:
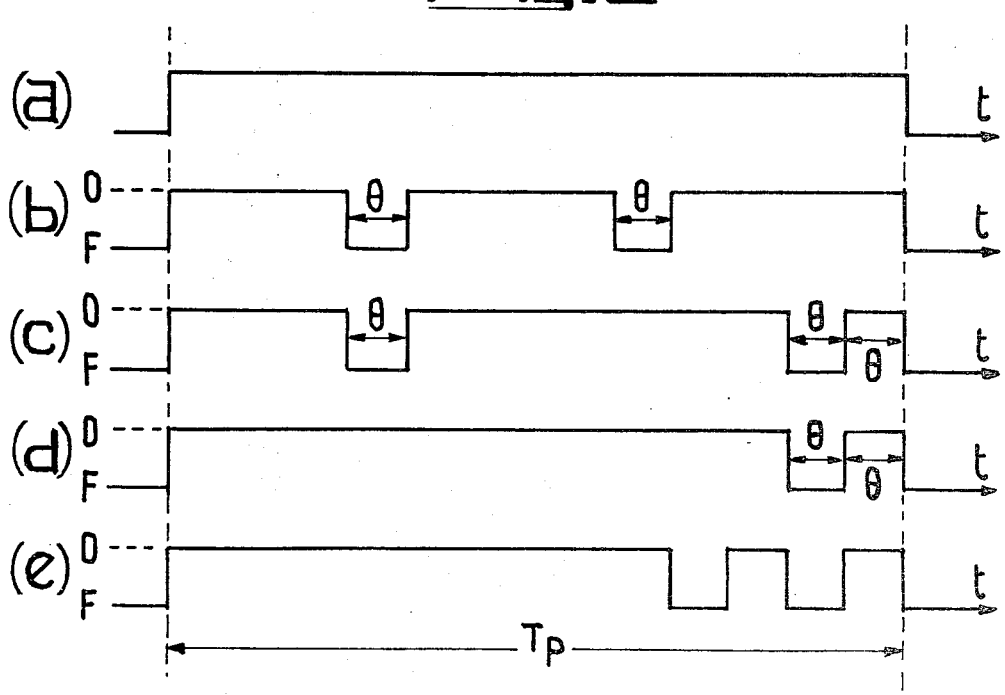

Further objects, features and advantages of the invention will be come apparent from the following description, given merely by way of example and is illustrated in the accompanying drawings in which:

FIG. 1 is a schematic sectional view of a preferred embodiment of a dust sampling device according to the invention; and FIG. 2 is a graph showing diagrammatically different methods of utilizing the device according to the invention.

FIG. 1 shows, schematically, a sampling tube which penetrates through the wall 1 of a chimney or an exhauts pipe 2 carrying a gas flow containing dust or powder for discharging it into the atmosphere, for example. The sampling tube used here is of a conventional type and it comprises a tubular body 3 which conveys samples of the gases charged with dust taken by its inlet end, to a filter 4 which may be in the shape of a disc a cartridge or a band which is progressing automatically, (like a film in a camera) disposed in a filter carrier 5 remote from the inlet end. The gases are drawn from the pipe 2 toward the filter 4 by a pump 6 connected to the outlet end of the tubular body 3 of the sampling tube through a further tubular member 7 and the filter carrier 5.

The inlet prifice of the tube 3 extending into the pipe 2 is constituted by a nozzle 8 having an inlet cross-section whose diameter is defined with precision and whose profile is chosen so as to avoid excessive perturbing of the gas flow in the pipe 2, which would render the measurement false, as well as to avoid differentiating between the dust particles according to their diameters. An outer tubular body 9 surrounds the sampling tube 3 for reinforcing and protecting it. This sampling tube 3 is relatively fragile and is usually provided with a device 10 for heating its walls (such as a helical tube carrying a heating fluid or a resistance), the heating device 10 is rendered necessary by the high temperature prevailing in the chimney 2 and by the high proportion of steam usually found therein. The dimensions of the component parts of the sampling tube 3 and the shape of the tube 7 which connects it to the filter carrier 5, may vary and depend in particular on the types of pipe or chimney 2 to be inspected.

The sampling device described heretofore is absolutely conventional (prior art). It operates in the following manner: in a first pumping or sampling phase, the pump 6 operates and the gases contained in the pipe 2 are drawn off by way of the sampling tube 3; in a second phase, termed measuring phase the pump 6 is stopped and the filter 4 is removed from its holder 5. The dust accumulated by the filter 4 during the sampling phase, is weighed. This results in the two aforementioned serious drawbacks: a portion part of the dust which should have been weighed remains in the tube 3; the tube 3 becomes soiled and may become clogged up.

The device according to the invention comprises means for closing the inlet orifice of the nozzle 8 which are, for example, constituted by a valve member 11 having a spherical profile and supported by a nacelle 12. The suspension of the valve member 11 in the nacelle 12 is sufficiently free to allow it to position itself suitably on the orifice of the nozzle 8 and to ensure a good sealing when closed (position shown in FIG. 1).

The valve member 11 may also have a conical or flat profile. It is sufficient that this valve member 11 produce a suitable closure of the nozzle 8. It will preferably be made from a metal when the temperature in the pipe 2 is high, of the order of 180° to 500° C. It may be constructed from a flexible or resileint material, such as a plastic material, for example, when it concerns lower temperatures.

The nacelle 12 has sidewalls which are large enough with respect to the valve member 11 to perform the function of a deflector and to protect the exterior of the nozzle against projections and deposits when the nozzle 8 is closed.

In the prefered embodiment illustrated here, the nacelle 12 is fixed to one end an arm 18 (lever) whose shape and dimensions depend on the dimensions of the sampling tube. Simple articulations (pivots), resistant to corrosion and high temperature, respectively connect the arm 18 to a support 14 and a control linkage (rod) 15. These articulations are conventional and such, for example, that when the rod 15 is shifted toward the right side, the nacelle 12 rises and closes the nozzle 8, whereas when the rod 15 is shifted toward the left the nacelle 12 side of the drawing, descends and opens the nozzle 8.

The control linkage 15 is actuated by driving means 16 which is preferably constituted by a pneumatic jack but which may also be in the form of an electromagnet or a motor. These driving means 16 are controlled, as will now be explained, by a control circuit 17.

The diagram (a) in FIG. 2 illustrates, as a function of time t, the gas flow in the sampling tube, which is substantially constant throughtou the duration Tp of a sampling period while the pump 6 operates and zero before and after this period, when the pump 6 is stopped and there is no suction. The duration Tp of the sampling phase may differ according to the desired type of measurement.

Diagrams (b), (c), (d), and (e) of FIG. 2 illustrate diagrammatically, but not to scale, a certain number of possibilities of utilization of the closing device according to the invention, for preventing the deposition on the sampling tube walls of the portion of the sampled dust.

The value F of these graphs corresponds to the open position of the valve 11 when the orifice of the nozzle 8 is left free whereas the value O corresponds to the closed position of the valve 11.

In all the cases illustrated here, the nozzle orifice or snout is always closed when there is no pumping, that is to say, outside the sampling period Tp. This condition is not essential to the operation of the device of the invention, since the existence of the pneumatic shocks does not depend thereon; it is, however, preferable, since it permits avoiding the soiling of the snout and of the tube 3 by the dust which would otherwise penetrate at low velocity between two sampling periods Tp. This spurious penetration is source of error in the measurement, in particular in continuous monitoring devices which must operate without intervention during several months and the low velocity dust deposited at the snout of the sampling tube 3 may reduce the diameter thereof.

The diagram (b) illustrates a mode of operation which may be employed when the sampling period duration Tp is rather long, for example about 20 minutes. In this case, the nozzle 8 may suddenly be closed by the valve 11 for relatively short periods of time $\theta$ (for example, less than 0.1Tp) so as to create a pneumatic shock, several times per sampling period Tp, for example every 5 minutes.

The pneumatic shock thus produced in the tube, where the suction always occurs, has for effect to empty the tube of the dust which are still in suspension and to produce a suction force which detaches the dust which are freshly deposited on the heated walls before they have time to adhere thereto.

The diagram (c) illustrates a mode of operating the device of the invention which is even more effective than that of the diagram (b). It consist of terminating the sampling period Tp successively by a brief closure period followed by a brief opening of duration $\theta$, for example, before its end at Tp. The pneumatic shock is produced here at the end of the sampling period, which is the optimum condition of operation.

The diagram (d) illustrates the same mode of operating as (c) as concerns the terminal portion of the sampling phase-brief closuren brief opening. This mode of operation concerns a much shorter period Tp, where it is sufficient to produce a single pneumatic shock.

The line (e) illustrates a mode of operation in which the sampling period terminates in a plurality of successive terminal cycles including a brief closure followed by a brief opening. The number of cycles (here two of them) depends on the length of the sampling period, the concentration of dust, temperature and humidity of the exhaust gases as well as other parameters which can be determined experimentally.

What is claimed is:

1. A method of sampling a dust laden atmosphere within an enclosure, the steps comprising:
   providing an elongated small diameter sampling tube extending from within the enclosure to a point exterior thereof;

providing a filter element exterior to said enclosure and coupled to said tube;

establishing a vacuum within said tube for a time T to induce flow of a sample of the dust laden atmosphere from the enclosure through said tube to impinge on said filter; and suddenly closing the inlet end of said sampling tube within said enclosure at least once while maintaining the interior of the tube under vacuum in order to produce at least one pneumatic shock in said tube to prevent deposition of dust particles on the interior wall of said tube, the time of closure being very small compared to T.

2. A method as defined by claim 1 wherein said last step is performed close to the end of the time T.

3. A method as defined by claim 1 including the step of at least once briefly reopening the inlet end of said sampling tube after closing.

4. A method as defined by claim 3 in which the end of said brief reopening coincides with the end of the time T.

5. A method as defined by claim 3 in which during the time T, the inlet end of said tube is briefly opened and closed a plurality of times to create a plurality of pneumatic shocks during the time T.

* * * * *